US006439235B1

(12) United States Patent
Larquet et al.

(10) Patent No.: US 6,439,235 B1
(45) Date of Patent: Aug. 27, 2002

(54) OXYGEN THERAPY EQUIPMENT WITH A DEVICE FOR RESPIRATORY ASSISTANCE WITHOUT A NOSE TUBE

(75) Inventors: Christian Larquet, Guyancourt; Bruno Marie, Montigny le Bretonneux; Alain Villermet, Viroflay, all of (FR)

(73) Assignee: L'Air Liquide, Societe Anonyme a Directoire et Conseil de Surveillance pour l'Etude et l'Exploitation des Procedes Georges Claude, Paris (FR)

( * ) Notice: Subject to any disclaimer, the term of this patent is extended or adjusted under 35 U.S.C. 154(b) by 0 days.

(21) Appl. No.: 09/645,444

(22) Filed: Aug. 25, 2000

(30) Foreign Application Priority Data

Aug. 30, 1999 (FR) .............................. 99 10905

(51) Int. Cl.[7] ........................... A61M 15/08; A61B 7/00
(52) U.S. Cl. ............................. 128/207.18; 128/203.18; 128/206.18; 128/207.13; 128/203.22
(58) Field of Search ....................... 128/203.18, 206.18, 128/207.13, 207.18, 203.22, 206.11

(56) References Cited

U.S. PATENT DOCUMENTS

| 4,406,283 A | | 9/1983 | Bir |
| 4,559,941 A | | 12/1985 | Timmons et al. |
| 4,660,555 A | * | 4/1987 | Payton .................. 128/207.18 |
| 4,708,446 A | * | 11/1987 | Timmons et al. ............ 351/158 |
| 4,742,824 A | * | 5/1988 | Payton et al. ........... 128/207.18 |
| 4,808,160 A | * | 2/1989 | Timmons et al. ............. 604/94 |
| 4,858,476 A | * | 8/1989 | Tobin ...................... 73/863.23 |
| 5,042,478 A | * | 8/1991 | Kopala et al. ......... 128/204.18 |
| 5,193,534 A | * | 3/1993 | Peppler ................. 128/207.18 |
| 5,558,090 A | * | 9/1996 | James ................... 128/207.18 |
| 5,575,282 A | * | 11/1996 | Knoch et al. .......... 128/204.18 |
| 6,189,870 B1 | * | 2/2001 | Withall ........................ 261/62 |

FOREIGN PATENT DOCUMENTS

| AU | 621 798 | 3/1992 |
| FR | 762 087 | 3/1934 |
| WO | WO 99/13929 | 3/1999 |

* cited by examiner

Primary Examiner—Aaron J. Lewis
Assistant Examiner—Darwin P. Erezo
(74) Attorney, Agent, or Firm—Young & Thompson

(57) ABSTRACT

A portable device for administering a gas. The device can supply at least one nostril of a user with at least part of a gas. The device includes at least one gas distribution nozzle and a support, with which the at least one gas distribution nozzle is supported or held in position on the face of the user. The at least one gas distribution nozzle is held along at least part of the outer wall or surface of the nose or cheeks of the user, when the device is positioned on the head or the face of the user. The at least one nozzle is outside the user's nostrils.

18 Claims, 5 Drawing Sheets

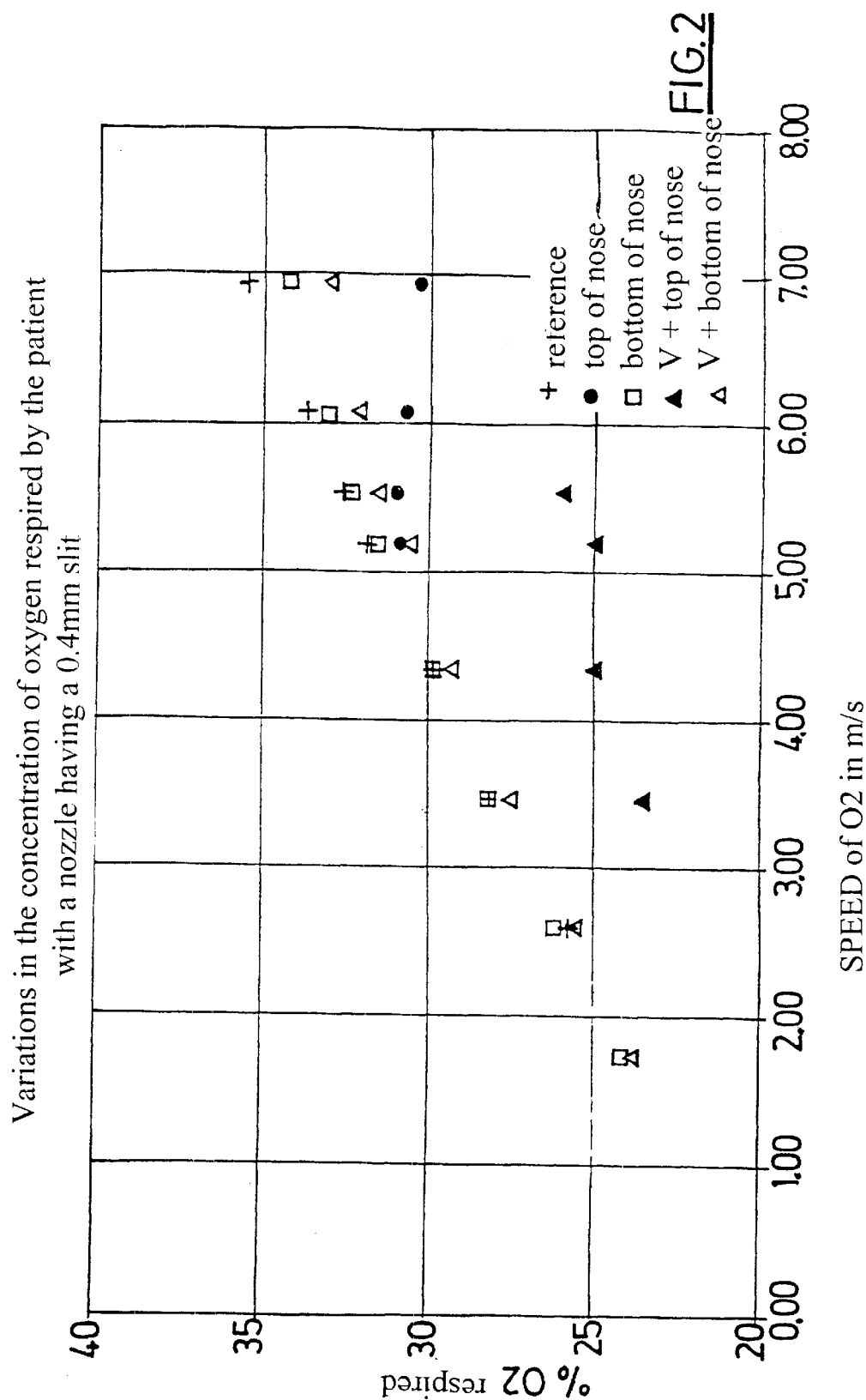

OXYGEN THERAPY EQUIPMENT WITH A DEVICE FOR RESPIRATORY ASSISTANCE WITHOUT A NOSE TUBE

BACKGROUND OF THE INVENTION

The invention relates to a device for administering a gas or a gaseous mixture, in particular oxygen, via the nasal route to a user, such as a patient, a sportsman or an airline pilot, for example.

As is known, in the medical field, devices for respiratory assistance generally comprise a generator of highly concentrated oxygen and nose tubes.

The generator can be either a cylinder containing oxygen of cryogenic and/or pharmaceutical quality, or an oxygen concentrator, such as a device with PSA (pressure swing adsorption) cycles, with which oxygen, having a purity of greater than 90%, can be produced from air.

On leaving the generator, the oxygen circulates through tubes having a length generally of about one to three meters, and is injected through a nozzle consisting of two small tubes of 10 to 12 mm in length, which are inserted into the nostrils so that the oxygen is inhaled by the patient.

In patients suffering from respiratory insufficiency, these small tubes have to be inserted into their nostrils for periods varying between 12 and 24 hours a day, depending on the severity of their condition.

However, the small tubes sometimes cause wounds or irritations on the inner nasal walls and these, under the added effect of the injection of highly concentrated oxygen ($\geq 90\%$) and the high speed of ejection of the gas, may become very painful.

SUMMARY OF THE INVENTION

The object of the present invention is therefore to solve the problem of effective administration of oxygen to a user, such as a patient, in particular a patient with serious respiratory insufficiency, which administration of oxygen does not damage the inner walls or nasal cavities of this user or patient, even when the latter has to be supplied with oxygen for long periods of time, which can be up to 24 hours a day.

The solution afforded by the present invention is therefore a portable device for administering a gas, which device can supply at least one nostril of a user with at least part of a gas, comprising at least one gas distribution nozzle and support means with which at least said gas distribution nozzle can be supported and/or held in position close to or in contact with the face of the user and along at least part of the outer wall or surface of the face situated near the nasal region of said user, when the device is positioned on the head and/or the face of said user.

The invention also relates to a portable device for administering a gas, which device can supply at least one nostril of a user with at least part of a gas, comprising at least one gas distribution nozzle and support means with which at least said gas distribution nozzle can be supported and/or held in position close to or in contact with the face of the user and along at least part of the outer nasal wall or surface of said user, when the device is positioned on the head and/or the face of said user.

Moreover, the invention also relates to a portable device for administering a gas, which device can supply at least one nostril of a user with at least part of a gas, comprising at least one gas distribution nozzle and support means with which at least said gas distribution nozzle can be supported and/or held in position close to or in contact with the face of the user and along at least part of the wall or surface of at least one of the cheeks of the user and close to the nasal region of said user, when the device is positioned on the head and/or the face of said user.

Depending on circumstances, the device according to the invention can comprise one or more of the following characteristics:

- At least one gas distribution nozzle is directed toward at least one nostril of the user and is positioned outside said at least one nostril, when the device is positioned on the head and/or the face of the user. In other words, according to the invention, the gas distribution nozzle or nozzles do not engage, even partially, in the user's nostrils. To put it another way, these nozzles are positioned in immediate proximity to the nostrils, that is to say to the nasal region, either on the cheeks, or on the longitudinal sides of the nose, and the gas flow delivered via the nozzles thus travels, at least temporarily and/or locally, outside said nostrils before passing into them upon inhalation of the gas by the user.
- It additionally comprises gas-directing means with which the gas can be directed to at least said distribution nozzle, said gas-directing means preferably comprising at least one gas channel.
- The gas-directing means comprise at least one supple or flexible channel, preferably at least one channel made of polymer.
- It comprises at least two gas distribution nozzles, said distribution nozzles preferably being arranged in such a way as to be positioned on either side of the nose of the user, along the outer wall of the nose.
- The gas-directing means comprise at least one multiple gas channel formed by an outer conduit and at least one inner conduit.
- The gas-directing means comprise at least one multiple gas channel formed by an outer channel and at least one inner channel which are concentric.
- The support means are chosen from the group consisting of glasses or half-glasses, devices in the shape of an artificial nose, headbands, and pince-nez devices.
- The nozzle or nozzles have a diameter or a width of between 0.2 mm and 25 mm, preferably of between 0.4 mm and 13 mm.
- The nozzle or nozzles have a gas outlet end of cylindrical, oval or flattened shape, preferably a flattened outlet end.

Furthermore, the invention also relates to a method for administering a gas or a gaseous mixture to a user via the nasal route, in which:

(a) said gas or gaseous mixture is directed to at least one gas distribution nozzle situated close to or in contact with the face of the user and arranged along at least part of the outer wall or surface of the face situated near the nasal region of said user, in particular along at least part of the outer nasal wall or along at least part of the wall or surface of at least one of the cheeks of the user and close to the nasal region of said user; and (b) at least one flow of said gas or gaseous mixture is delivered by means of said at least one distribution nozzle in the direction of at least one of the nostrils of the user, said flow of gas sweeping across at least part of the outer surface or wall of the face of the user, in particular at least part of the outer surface or wall of the nose or at least one of the cheeks of the user.

The gas or gaseous mixture is preferably oxygen or a gas containing oxygen.

The speed of the gas or gaseous mixture delivered via the distribution nozzle is advantageously between 0.1 m/s and 10 m/s, preferably lower than about 5 m/s.

The gaseous flow is preferably delivered via at least two distribution nozzles.

In addition, the invention also relates to equipment for administration of gas by inhalation, usable in particular in the medical field, comprising at least one gas source connected to at least one device according to the invention, means for regulating the gas flow rate preferably being arranged between said gas source and said device.

In particular, it additionally comprises gas humidification means arranged between the means for regulating the gas flow rate and the nozzle or nozzles.

The gas source is advantageously a gas container, preferably a gas cylinder, or an oxygen concentrator apparatus with which it is possible to produce oxygen, or a gas rich in oxygen, from air.

Indeed, while respecting the characteristics in terms of the flow rate and concentration of oxygen inhaled by a patient, the injection system according to the invention avoids any injury to the patient and most certainly affords a considerable improvement to the known devices and systems.

This is because the known administration devices traditionally comprise a system of injection nozzles with which it is possible to direct the jet of oxygen into the nostril or nostrils and, consequently, to control the flow of oxygen passing into the patient's airways.

The nozzles are usually tubes arranged inside the nostrils.

In order to avoid the abovementioned injuries inside the nasal cavity, it is possible to contemplate injecting the oxygen through nozzles placed outside the nostrils.

However, it is known that a jet of gas has a tendency to dissipate into the air as it travels, which fact leads to a decrease in its average speed and prevents it from reaching its target, either partially or completely.

Thus, a jet of oxygen injected into the air using a nozzle of any given shape can fully reach its "target", that is to say a nostril, only if it satisfies the conditions of being very fine, of always having a high speed, and of being injected very close to the nostril.

This can therefore only be achieved with a very fine nozzle placed at the entry to the nostril, in accordance with the known prior art.

The jet of oxygen, whose speed is necessarily high in order to reach the target, can rebound off the nasal walls if the nozzle is poorly oriented, resulting in a loss of oxygen and especially in poor control of the quantity inhaled.

In any event, the sensation of inhaling a jet of gas injected at high speed directly into the nostrils is very unpleasant.

This, however, does not happen with the device according to the invention.

In fact, the studies carried out by the inventors show that, by virtue of the device according to the invention, it is possible to apply a jet of gas along a convex wall constituted, for example, by the outer wall of the nostril or nostrils, in such a way that it follows this wall as far as the inside of the nostril and can be inhaled by the user or, according to another example, along the outer wall or surface of the cheek situated in proximity to the nostril or nostrils.

To do this, the characteristics of the jet must be within a very precise range, particularly in terms of speed and dimensions.

Consequently, the inventors of the present invention have shown that a parietal jet of oxygen injected, for example, along the nose (and not directly inside the nostrils), can, if it is properly oriented and if its characteristics conform with the curvatures of the nose, reach the nostrils in its entirety and be inhaled by the patient or user.

Such a solution makes it possible, at one and the same time, to avoid introducing tubes into the nostrils and to control the flow rate of oxygen inhaled by the patient or user, thereby effectively solving the problem set out above.

BRIEF DESCRIPTION OF THE DRAWINGS

The present invention will now be better understood on the basis of an illustrative embodiment and the attached figures, which are given by way of example and are non-limiting.

FIG. 2 is a graph showing percent of oxygen inhaled by a user as a function of the speed of injection of the oxygen;

DETAILED DESCRIPTION OF THE PREFERRED EMBODIMENTS

Figure 1:
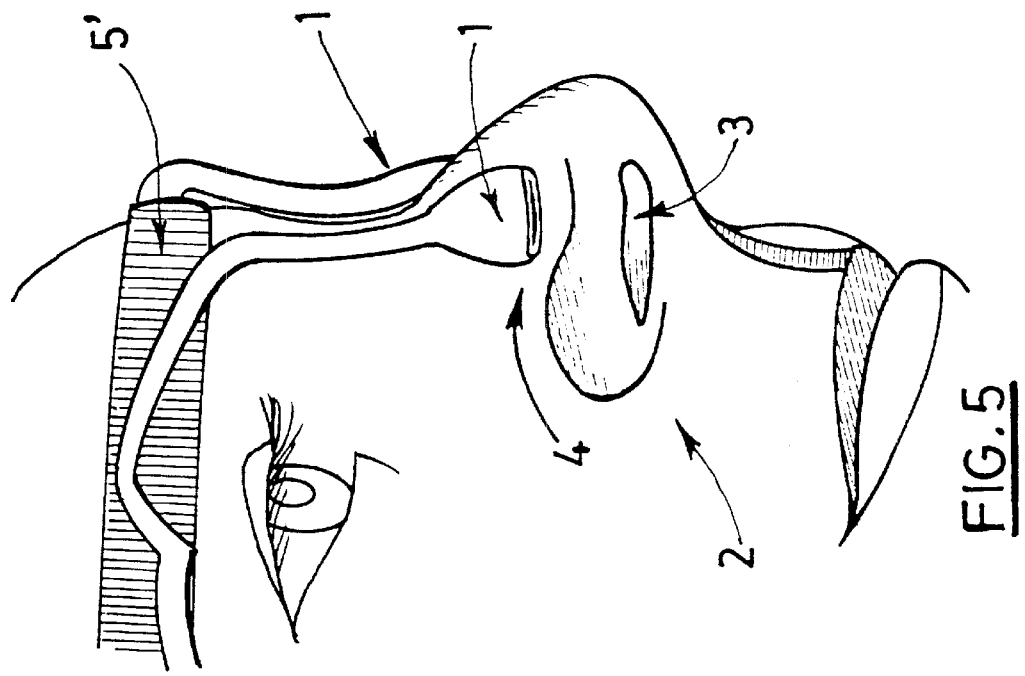
FIG. 1 shows a gas administration device according to a first embodiment.
Figure 5:
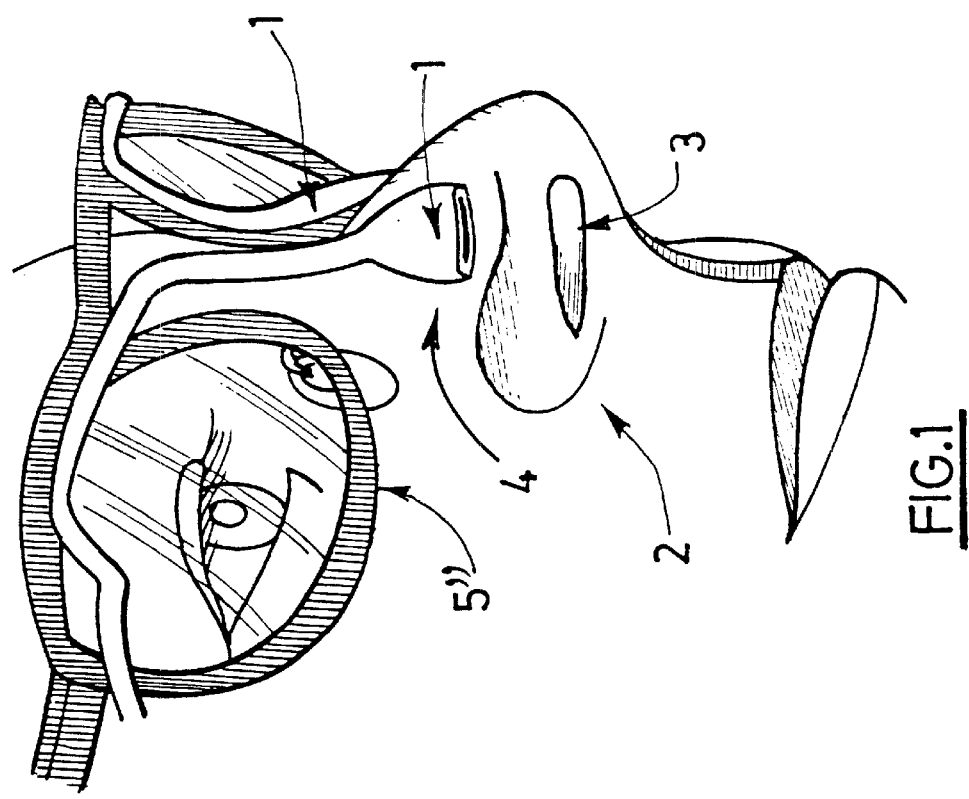
FIG. 5 shows a gas administration device according to a fourth embodiment.

FIGS. 1 and 3 through 5 are sketches showing a gas administration device according to the invention, comprising two nozzles 1 for injecting oxygen to a user 2.

As can be seen, the nozzles 1 are arranged along the outer wall 4 of the nose of the user 2, and on either side thereof, that is to say on each side of the bridge of the nose, and they are held in position there by suitable support means, such as one or more straps or a headband 5' (FIG. 5), a structure or a frame which can be positioned on the user's head, a device in the form of glasses 5" (FIG. 1) or half-glasses (FIGS. 3 and 4) bearing on the ears and/or the nose of the user 2, or similar.

According to another embodiment (not shown), the nozzle can also be made integral with a device of the "false nose" type, that is to say an artificial nose substituting either at least the lower part of the outer wall or surface of the nose, that is to say the region situated at the end of the nose near the nostrils, or at least the upper part of the outer wall or surface of the nose, that is to say the region situated at the root of the nose and between the eyes, so as to make it possible, in both cases, to standardize the characteristics and orientation of the nozzle or nozzles regardless of the shape of the patient's nose.

The false nose can incorporate the nozzles, that is to say these can be fixed to this false nose or made integral in the actual structure thereof, directly by casting for example.

The oxygen injected, substantially from the top downward, travels along the outer wall 4 of the nose before passing inside the nose via the nostrils 3.

In order to check the effectiveness of the device according to the invention, a study was carried out to determine the conditions for achieving complete control of the quantity of oxygen inhaled.

To do this:

The face of the user was simulated using a mask reproducing a human face;

The nostrils of the mask were fitted with tubes connected to a pump and an oxygen analyzer, making it possible both to simulate the user's breathing and to establish the quantity of oxygen actually inhaled;

An injection nozzle was placed at different positions on the nose in order to determine the necessary precision of positioning and its influence on the quantity of oxygen inhaled;

A Maintaining a constant rate of breathing, namely a rate simulating the rate of human breathing during the inhalation phase, that is to say approximately 24 l/min. The injection rate was modified over time and different nozzle dimensions were tested in order to detemine the range of functioning (dimensions, speed) within which all the injected oxygen is inhaled;

Finally, a ventilator placed at varying distances from the mask made it possible to study the attachment and the control of the jet of oxygen under external atmospheric conditions (presence of wind).

The results obtained show that it is possible to effectively control the flow rate of inhaled oxygen when the speed of the gas is maintained at less than 10 m/s, preferably less than about 5 m/s.

Above this level, some of the injected oxygen is not inhaled by the patient.

Nevertheless, in all cases the greater part of the injected oxygen is inhaled by the patient.

An important observation concerns the presence or absence of wind.

Thus, in the absence of a ventilator simulating the wind, the position of the injection nozzle on the nose has only a very slight influence on the performance of the system.

By contrast, in the presence of wind (of the order of several m/s), that is to say a ventilator placed at 1.50 meters, for example, control is poor if the nozzle is placed at the top of the nose (at the level of the supports of the glasses type). However, if the nozzle is placed at the lower part of the nose, control is perfect up to about 5 m/s.

Figure 4:
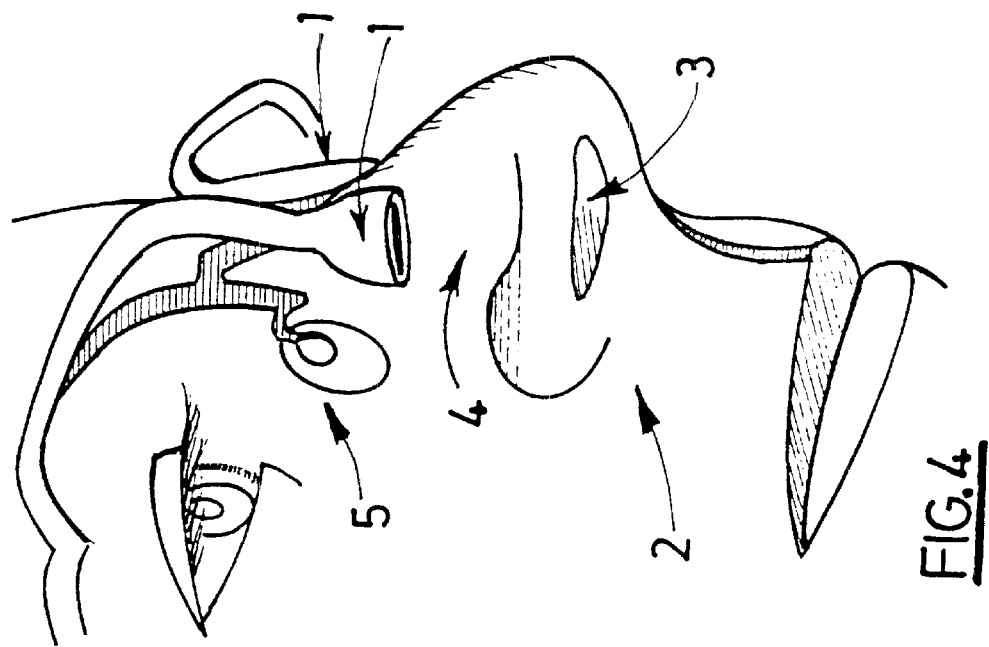
FIG. 4 shows a gas administration device according to a third embodiment.
Figure 3:
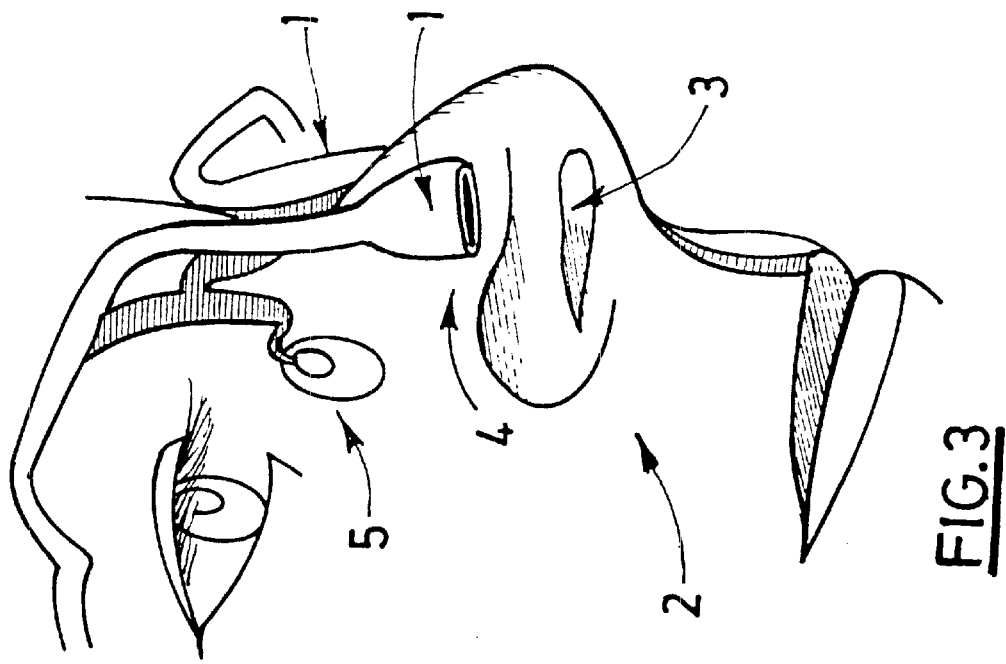
FIG. 3 shows a gas administration device according to a second embodiment.

FIG. 2, attached, shows clearly the percentage of oxygen inhaled by the user, simulated by the pump/oxygen analyzer system, as a function of the speed of injection of the oxygen for the different configurations represented in FIGS. 3 an 4:

Reference: corresponds to the percentage of oxygen obtained when the injection of oxygen is effected inside the actual inhalation tube. This reference corresponds to an inhalation of 100% of the injected oxygen;

Top of nose: the injection nozzle is placed at the top part of the nose, at the position where supports of the glasses type are normally situated (FIG. 4);

Bottom of nose: the injection nozzle is placed at the bottom part of the nose, at the site of the curvature of the vertical wall of the nose (FIG. 3);

V+Top of nose: the injection nozzle is placed at the top part of the nose in the presence of a ventilator placed at about 1.50 meters;

V+Bottom of nose: the injection nozzle is placed at the bottom part of the nose in the presence of a ventilator placed at about 1.50 meters.

FIG. 2 confirms that it is possible to effectively control the flow rate of oxygen inhaled by the patient when the nozzle is placed at the bottom part of the nose, even in the presence of a strong wind.

The nozzle is the same for all these configurations, that is to say a nozzle of flattened shape, the height of its outlet slit being 0.4 mm and its width about 1.25 cm. The flow rate corresponding to about 5 m/s (the limit speed for complete control) is 1.5 l/min for each nozzle. The trials on other slit heights are similar and the limit speed always appears to be situated toward about 5 m/s.

This last observation is important since it implies that the results presented can be obtained with very different flow rates, the speed of the injected oxygen being the important parameter in this system, on condition that the injected jet remains sufficiently fine to behave as a parietal jet.

Thus, with a nozzle slit of 0.8 mm in height and about 1.25 cm in width, complete control of oxygen inhaled by the user was achieved up to a flow rate of about 3 l/min for each nozzle and for a limit speed of about 5 m/s.

Figure 6:
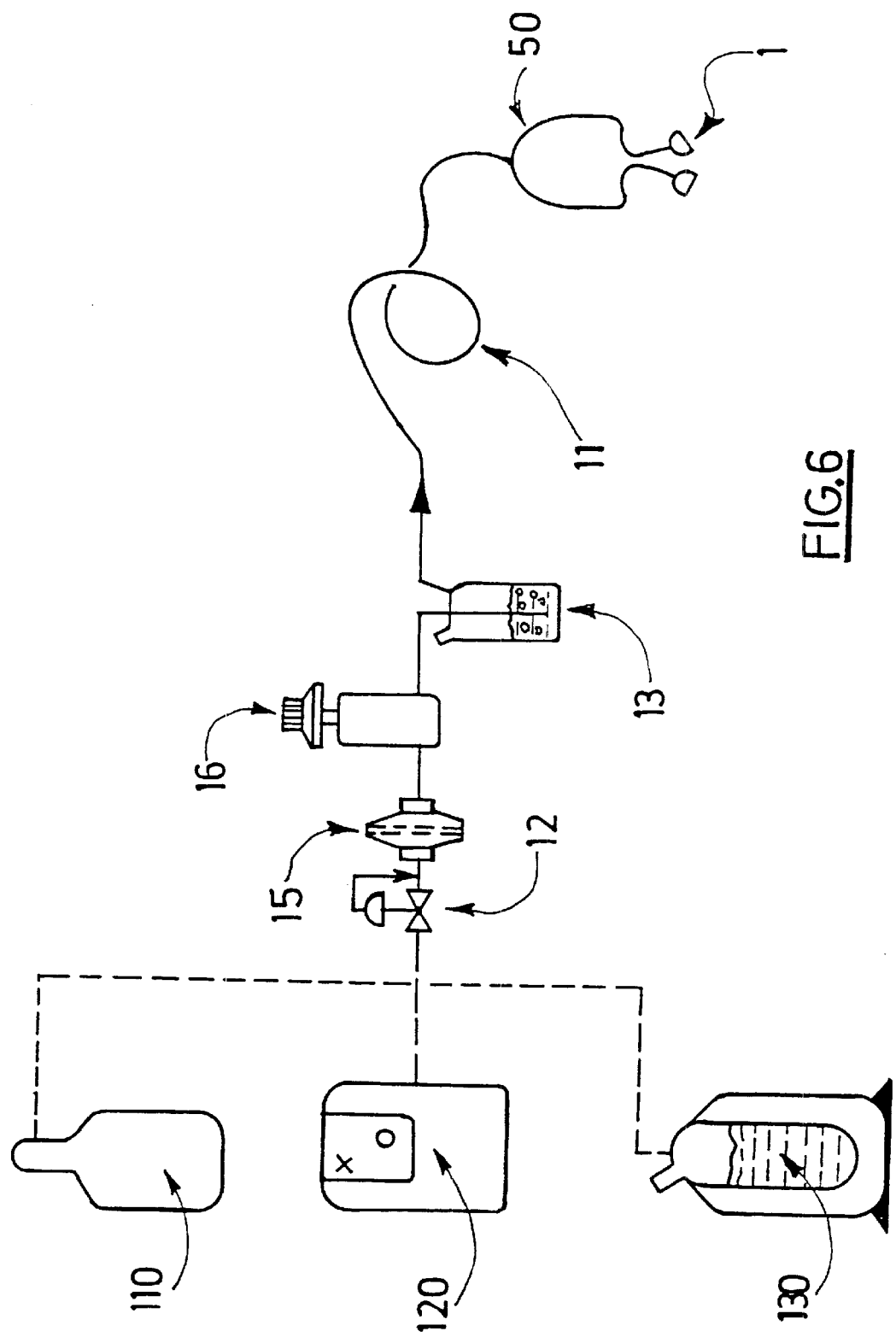
FIG. 6 shows oxygen therapy equipment according to the invention.

FIG. 6 for its part shows oxygen therapy equipment according to the invention, comprising a gas source which can be: either a gaseous oxygen cylinder 110, a generator of oxygen-enriched air, that is to say an oxygen concentrator 120, or a container holding liquid oxygen 130.

This gas source is connected by way of a gas channel 11 to a device according to the invention, as shown in FIGS. 1 and 3 through 5.

It will be seen from FIG. 6 that pressureregulating means, such as a gas pressure reducer 12, and means for regulating the gas flow rate, such as a flow rate selector 16, are arranged between the oxygen source and the device according to the invention.

In addition, one will also note the possible presence, on line 11, of a bacteriological filter 15 and of a gas humidifier 13 situated between the gas pressure reducer 12 and the device 50 with nozzles 1 according to the invention.

Figure 7:
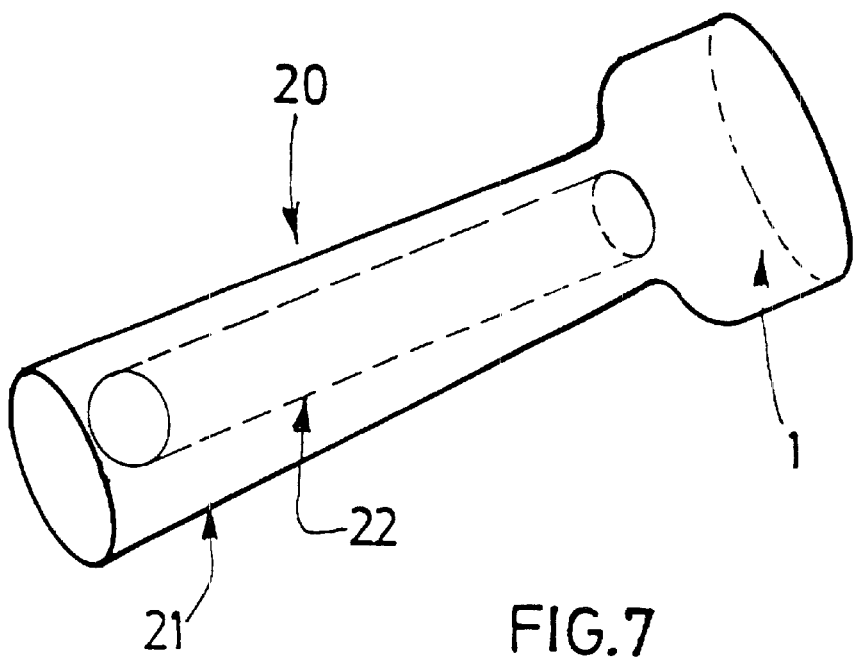
FIG. 7 shows a first nozzle embodiment including gas supply channels.

In addition, FIG. 7 shows a diagrammatic representation of a particular embodiment of the invention, according to which the gas distribution nozzle 1 is supplied with two gases of a different nature and/or composition which are directed along a multiple channel 20 formed, for example, by an outer conduit 21 and an inner conduit 22, in such a way as to allow different gases to be administered to the user.

Figure 8:
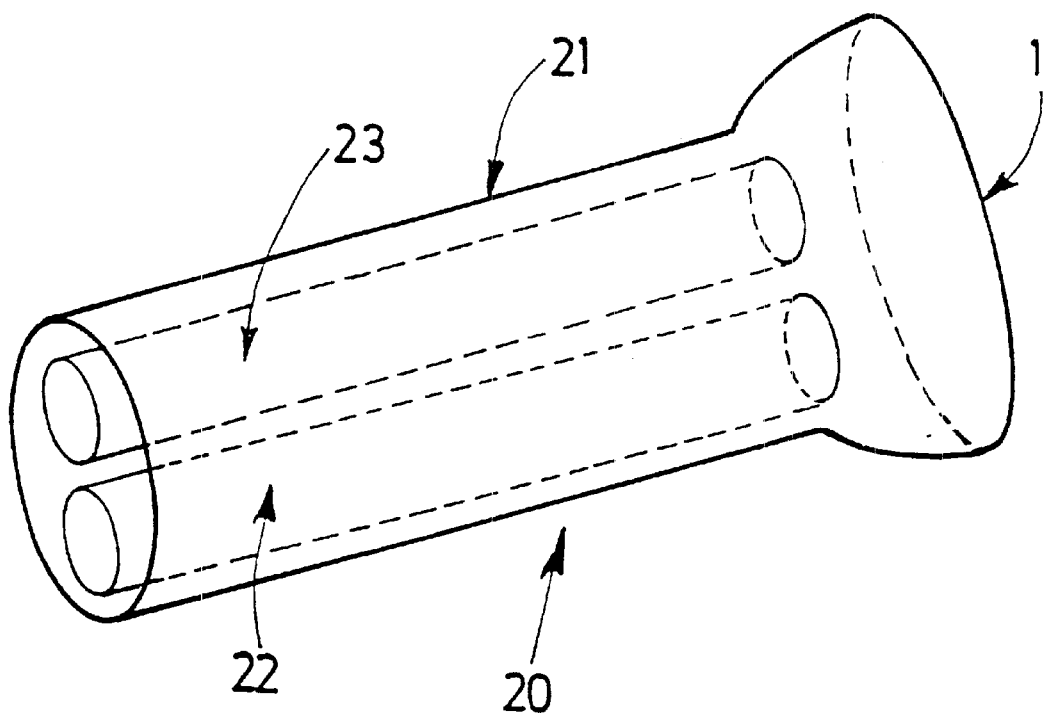
FIG. 8 shows a second nozzle embodiment including gas supply channels.

FIG. 8 is similar to FIG. 7, except that in this case the nozzle 1 is supplied with gas via a multiple channel 20 formed by an outer conduit 21 and several inner conduits 22 and 23 which are juxtaposed and/or concentric.

The invention is particularly suitable for the medical field, but it can also be used for other purposes, for example in sports or aeronautics, when a sportsman or an airline pilot may temporarily require oxygen assistance.

What is claimed is:

1. A device for providing gas to the nostrils of a user, comprising:

two gas distribution nozzles; and means for supporting said two gas distribution nozzles, said means for supporting holding said two gas distribution nozzles close to or in contact with a face of the user and along at least part of an outer surface of a nose of the user, when the device is positioned on a head of a user, said two gas distribution nozzles having gas exits spaced from a nostril of a user when the device is positioned on a head of the user so that after the gas exits each of said two gas distribution nozzles, the gas follows along the outer nasal wall of the nostrils of the user before the gas enters the nostrils.

2. The device as claimed in claim 1, further comprising gas-directing means with which the gas can be directed to said two gas distribution nozzles, said gas-directing means comprising at least one gas channel.

3. The device as claimed in claim 2, wherein said at least one gas channel is flexible.

4. The device as claimed in claim 2, wherein said gas-directing means comprises at least one multiple gas channel having an outer conduit and at least one inner conduit.

5. The device as claimed in claim 1, wherein said two gas distribution nozzles are arranged on either side of the nose of the user along an outer wall of the nose.

6. The device as claimed in claim 1, wherein said means for support are chosen from the group consisting of glasses, half-glasses, devices in the shape of an artificial nose, headbands, and pince-nez devices.

7. The device as claimed in claim 1, wherein said two gas distribution nozzles have a diameter between 0.2 mm and 25 mm.

8. The device as claimed in claim 1, wherein said two gas distribution nozzles have a gas outlet end having one of a cylindrical, oval and flattened shape.

9. Equipment for administration of gas by inhalation, comprising:
   at least one gas source connected to at least one device as claimed in claim 1; and
   means for regulating a gas flow rate between said gas source and said device.

10. The equipment as claimed in claim 9, further comprising gas humidification means between said means for regulating a gas flow rate and said two gas distribution nozzles.

11. The equipment as claimed in claim 9, wherein the at least one gas source is one of a gas container and an oxygen concentrator apparatus that produces a gas rich in oxygen from air.

12. A method for administering a gas to a user via a nasal route, comprising the steps of:
   directing the gas to two gas distribution nozzles situated close to or in contact with a face of the user and arranged along at least part of an outer nasal wall of a nose of the user; and
   delivering the gas through the two distribution nozzles in the direction of the nostrils of the user, the gas exiting the two gas distribution nozzles before reaching the nostrils and sweeping across at least part of the outer nasal wall of the nose of the user,
   the gas following along the outer nasal wall of each of the nostrils of the user before entering inside the nostrils.

13. The method as claimed in claim 12, wherein the gas is a gas containing oxygen.

14. The method as claimed in claim 12, wherein a speed of the gas delivered in said delivering step is between 0.1 m/s and 10 m/s.

15. The method as claimed in claim 14, wherein the speed of the gas is less than about 5 m/s.

16. A portable device for delivering a gas to a user from outside of nostrils of the user comprising:
   at least one nozzle for delivering the gas to the user;
   at least one supply line for supplying the gas from a supply source to said at least one nozzle; and
   means for attaching said at least one supply line to the user to stabilize the supply line,
   wherein the gas exits an end of said at least one nozzle outside the nostrils and flows along an outer wall of a nose of the user before entering the nostrils, and
   wherein said at least one supply line is attached to a bridge of a nose of the user.

17. The portable device as claimed in claim 16, wherein the diameter of the at least one nozzle is between 0.4 mm and 13 mm.

18. The portable device as claimed in claim 16, wherein the supply line comprises at least one multiple gas channel having an outer conduit and at least one inner conduit.

* * * * *